(12) United States Patent
Antros

(10) Patent No.: US 10,478,375 B2
(45) Date of Patent: Nov. 19, 2019

(54) PULMONARY EXPANSION THERAPY DEVICES

(71) Applicant: Peter Antros, Bourbonnais, IL (US)

(72) Inventor: Peter Antros, Bourbonnais, IL (US)

(73) Assignee: Peter Antros, Bourbonnais, IL (US)

( * ) Notice: Subject to any disclaimer, the term of this patent is extended or adjusted under 35 U.S.C. 154(b) by 1090 days.

(21) Appl. No.: 14/865,814

(22) Filed: Sep. 25, 2015

(65) Prior Publication Data

US 2017/0087054 A1 Mar. 30, 2017

(51) Int. Cl.
*A61H 9/00* (2006.01)
*A61H 31/02* (2006.01)
*A61H 23/00* (2006.01)

(52) U.S. Cl.
CPC ............ *A61H 31/02* (2013.01); *A61H 9/0057* (2013.01); *A61H 23/006* (2013.01);
(Continued)

(58) Field of Classification Search
CPC ........ A61H 9/00; A61H 9/005; A61H 9/0057; A61H 23/04; A61H 2201/1238;
(Continued)

(56) References Cited

U.S. PATENT DOCUMENTS 2,223,570 A * 12/1940 McMillin ................ A61H 31/02
137/104
2,579,209 A * 12/1951 Smith .................... A61H 9/005
601/151
(Continued)

FOREIGN PATENT DOCUMENTS

WO 2012177152 A1 12/2012

OTHER PUBLICATIONS

Ventquest. GHIA 2016. LifeVest: Helping Babies Breathe. Sep. 15, 2016. (URL: http://www.ventquest.ca/ghia-2016-day1-science-pitches-lifevest-helping-babies-breathe/).
(Continued)

*Primary Examiner* — Michael J Tsai
(74) *Attorney, Agent, or Firm* — Beem Patent Law Firm

(57) ABSTRACT

A pulmonary expansion therapy (PXT) device may be a handheld device that covers specific lung fields and may generate negative pressure fields locally. The device also may provide percussion therapy for airway clearance. The PXT may generate a localized negative pressure field non-invasively to the exterior of the chest wall, thereby increasing the functional residual capacity in underlying lung fields. As a result, increased ventilation and perfusion to the targeted internal lung field may be achieved by creating a decrease in the external barometric pressure relative to the more positive intrinsic airway pressures. The PXT device also may improve lung compliance by enabling a medical professional such as a Respiratory Therapist/Care provider to grab and elevate the chest wall to compensate for the dysfunction of the respiratory musculature responsible for lifting the chest wall during normal breathing. In some embodiments, once a targeted functional residual capacity (FRC) has been established, percussion may be applied with increased effectiveness due to greater oscillatory movement of chest wall.

20 Claims, 14 Drawing Sheets

(52) U.S. Cl.
CPC .................. *A61H 2031/025* (2013.01); *A61H 2201/0157* (2013.01); *A61H 2205/084* (2013.01)

(58) Field of Classification Search
CPC ............ A61H 2201/1246; A61H 7/008; A61H 2031/001; A61H 31/02; A61H 2031/025
See application file for complete search history.

(56) References Cited

U.S. PATENT DOCUMENTS

| | | | | |
|---|---|---|---|---|
| 2,626,601 | A * | 1/1953 | Riley | A61H 9/005 137/565.27 |
| 2,629,372 | A * | 2/1953 | Wallin | A61H 31/02 601/44 |
| 2,665,145 | A * | 1/1954 | Shumaker | F16L 27/023 285/121.7 |
| 2,853,998 | A * | 9/1958 | Emerson | A61H 31/02 601/44 |
| 3,078,842 | A * | 2/1963 | Gray | A61H 9/0078 601/44 |
| 3,315,665 | A * | 4/1967 | MacLeod | A61H 9/005 601/7 |
| 3,955,563 | A | 5/1976 | Maione | |
| 4,257,407 | A | 3/1981 | Macchi | |
| 4,667,672 | A * | 5/1987 | Romanowski | A61B 17/12 128/DIG. 20 |
| 4,977,889 | A | 12/1990 | Budd | |
| 5,358,467 | A * | 10/1994 | Milstein | A61H 9/005 601/10 |
| 5,453,081 | A | 9/1995 | Hansen | |
| 5,537,999 | A | 7/1996 | Dearman et al. | |
| 5,573,498 | A | 11/1996 | Hayek | |
| 5,645,522 | A | 7/1997 | Lurie et al. | |
| 5,727,569 | A | 3/1998 | Benetti et al. | |
| 5,988,166 | A | 11/1999 | Hayek | |
| 6,345,618 | B1 | 2/2002 | Hayek | |
| 6,357,441 | B1 | 3/2002 | Kwok et al. | |
| 7,594,508 | B2 | 9/2009 | Doyle | |
| 8,281,641 | B1 | 10/2012 | Wooten et al. | |
| 8,579,837 | B1 * | 11/2013 | Makower | A61H 19/34 601/6 |
| 2003/0083554 | A1 | 5/2003 | Paolitto et al. | |
| 2005/0085799 | A1 | 4/2005 | Luria et al. | |
| 2005/0126578 | A1 | 6/2005 | Garrison et al. | |
| 2005/0222544 | A1 * | 10/2005 | Weston | A61M 1/0001 604/313 |
| 2005/0234289 | A1 | 10/2005 | Anstadt et al. | |
| 2008/0086065 | A1 | 4/2008 | Holm et al. | |
| 2008/0115786 | A1 | 5/2008 | Sinderby et al. | |
| 2009/0082741 | A1 | 3/2009 | Hu | |
| 2011/0118683 | A1 * | 5/2011 | Weston | A61F 5/048 604/319 |
| 2012/0247479 | A1 | 10/2012 | Varga et al. | |
| 2012/0302910 | A1 | 11/2012 | Freeman et al. | |

OTHER PUBLICATIONS

Notification of Transmittal of the International Search Report and Written Opinion dated Aug. 29, 2016, issued in International Application No. PCT/US 16/49305 (14 pages).

* cited by examiner

PULMONARY EXPANSION THERAPY DEVICES

BACKGROUND OF THE INVENTION

1. Technical Field

The present application relates to medical devices for the treatment of atelectasis/airway collapse (AAC).

2. Related Art

Physiologic breathing in healthy individuals is accomplished by maintaining a negative pressure field inside the pleural cavity. This negative pressure field is enhanced by the downward motion of the diaphragm and upward and outward motion of the rib cage resulting in inspiration. Relaxation of these muscles results in exhalation which is passive, requiring no energy. The apexes of the lungs having a greater negative pressure than inferior lobes due to gravity's effect on lungs.

Atelectasis/airway collapse (AAC) is a serious medical problem that occurs in a number of respiratory conditions caused by a wide range of etiologies. AAC often results in respiratory impairment and/or failure. In a typical case, a patient experiencing AAC is treated with intubation and mechanical ventilation using positive pressure.

During positive pressure ventilation of sedated or paralyzed patients, airflow into the lungs takes the path of least resistance. In this scenario, the healthy section of lung presents the path of least resistance as the collapsed and/or obstructed airway restricts airflow. This phenomena is problematic as the medical professional must carefully recruit the atelectatic or sick lung fields without overinflating and thereby damaging the healthy lung.

This problem is exacerbated by mechanical ventilation strategies, as recruitment usually involves increasing distending pressures either by increasing peak inspiratory pressures, or by delivering more volume. Both of these techniques increase the likelihood of barotrauma from over inflation of the healthier more compliant lung tissue.

To address these problems, negative pressure ventilators have been developed. For example, the earliest negative pressure ventilators developed at the turn of the 20th century relied on negative pressure via the "Iron Lung." In such a system, a patient is placed into a large steel chamber that forms a sealed, air-tight compartment around the patient's entire body with just their head outside the iron long as pumps periodically decrease and increase the air pressure within the chamber to cause the lungs to fill with or expel air to mimic the physiological action of breathing. Modern equivalents such as the Hayek Chest Cuirass (provided by Hayek Medical of London, England, UK) employ the same principle using a chest cuirass that covers the chest and abdomen.

While these negative pressure ventilators provide certain benefits, they also pose problems of their own. For example, blood pooling in organs such as the liver can occur due to the negative pressure field applied over the abdomen. In addition, because these devices rely on the formation of an air tight seal around the affected lung, they inhibit access to the patient. As another example, these devices are difficult to set-up and keep on a patient, which can be critical in an emergency care situation.

Accordingly, a need has long existed for improved systems and methods for lung expansion.

SUMMARY

A pulmonary expansion therapy (PXT) device may be a handheld device that covers specific lung fields and may generate negative pressure fields locally. The device also may provide percussion therapy for airway clearance. The PXT may generate a localized negative pressure field non-invasively to the exterior of the chest wall, thereby increasing the functional residual capacity in underlying lung fields. As a result, increased ventilation and perfusion to the targeted internal lung field may be achieved by creating a decrease in the external barometric pressure relative to the more positive intrinsic airway pressures. The PXT device also may improve lung compliance by enabling a medical professional such as a Respiratory Therapist/Care provider to grab and elevate the chest wall to compensate for the dysfunction of the respiratory musculature responsible for lifting the chest wall during normal breathing. In some embodiments, once a targeted functional residual capacity (FRC) has been established, percussion may be applied with increased effectiveness due to greater oscillatory movement of chest wall.

Other systems, methods, features and technical advantages of the invention will be, or will become apparent to one with skill in the art, upon examination of the figures and detailed description. It is intended that all such additional systems, methods, features and technical advantages be included within this summary and be protected by the claims.

BRIEF DESCRIPTION OF THE DRAWINGS

The invention can be better understood with reference to the following drawings and description. The components in the figures are not necessarily to scale, emphasis instead being placed upon illustrating the principles of the invention.

DETAILED DESCRIPTION OF THE PREFERRED EMBODIMENTS

The elements illustrated in the figures interoperate as explained in more detail below. Before setting forth the detailed explanation, however, it is noted that all of the discussion below, regardless of the particular implementation being described, is exemplary in nature, rather than limiting.

Figure 1:
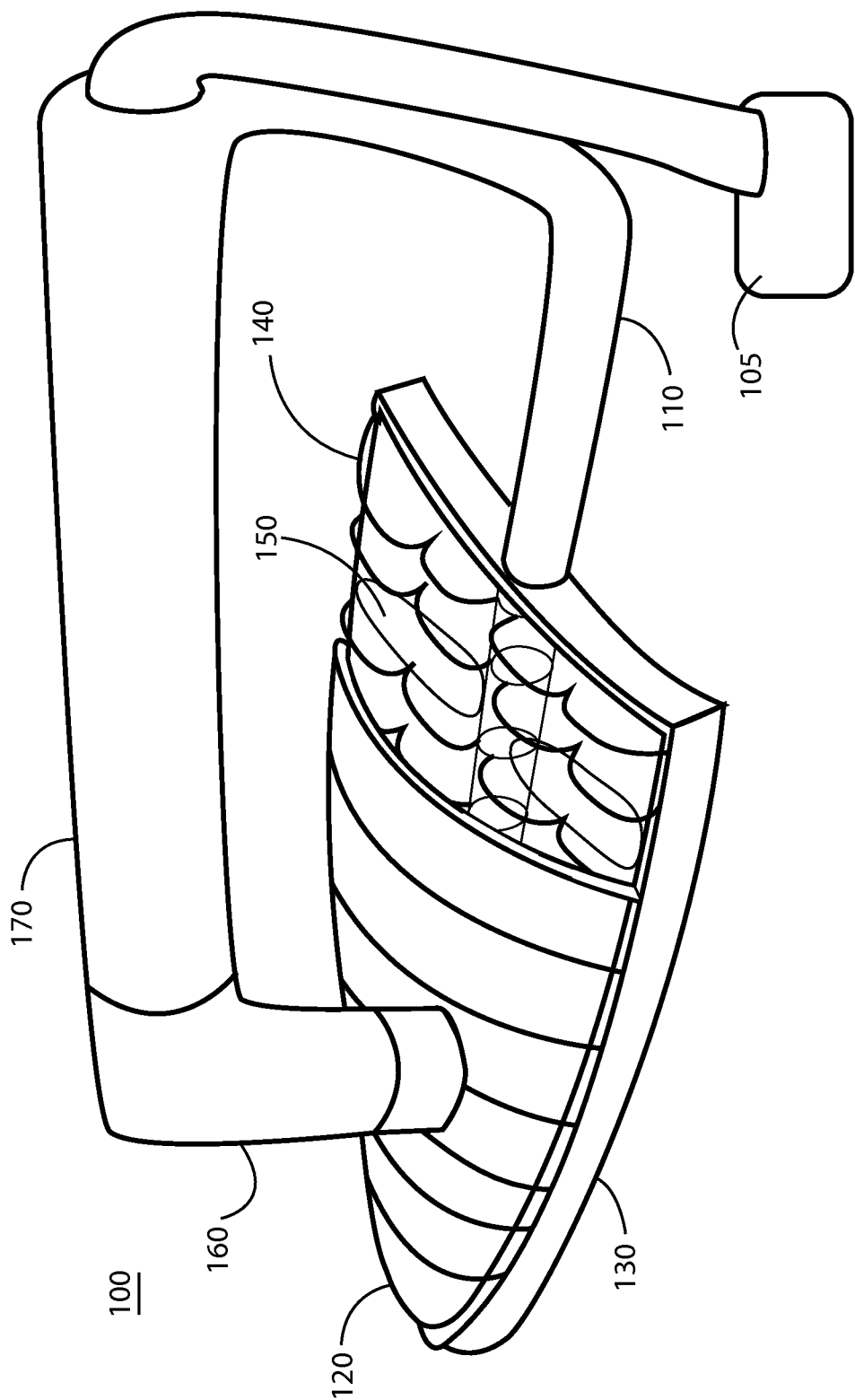
FIG. 1 shows a perspective view an exemplary pulmonary expansion therapy (PXT) device.

Referring to the drawings, and initially to FIG. 1, an exemplary pulmonary expansion therapy (PXT) device 100 is shown. In the illustrated embodiment, the PXT device 100 may include an inflow tube 110, an outer shell 120, a membrane 130, one or more negative pressure lumens 140, one or more positive pressure chambers 150, an outflow tube 160, and a handle 170.

In some embodiments, the device 100 may also include an airflow source 105. For example, airflow source 105 may be a gas and/or vacuum source that provides pressures between about 10 pounds per square inch (PSI) to about 120 PSI, preferably between about 25 PSI and about 75 PSI and even more preferably between about 40 PSI to about 60 PSI. Alternatively, or additionally, an electric motor may be used to generate both the negative and positive pressures. This motor may be monitored and controlled electronically to establish and calculate negative pressures and the increased volumes being generated in the positive pressure chambers 150 and/or the negative pressure lumens 140. As illustrated, a single tube may connect air source 105 to the device 100. Alternatively, or additionally, multiple tubes may be provided to supply either positive air flow, negative air flow, or both (see, for example, FIG. 7).

Other airflow source that provide positive and/or negative pressures of other magnitudes may also be used. For example, in a hospital or home setting, a 50 psi O2 source may be used. In the home care setting, the same source may be used or a compressor may power the percussion. As another example, the negative pressure source gas may be a portable suction device. Alternatively, or additionally, the device 100 may be coupled to third-party airflow sources.

In operation, the inflow tube 110 may introduce air into the one or more positive pressure chambers 150 while the outflow tube 160 may provide a passage for the outflow of air from the one or more negative pressure lumens 140. The negative pressure lumens 140 may be coupled to the membrane 130 such that, when the device 100 is placed on a patient and as air flows through the device 100, suction is created causing the membrane 130 to adhere to the patient's skin. This results in the generation of a localized negative pressure at the exterior of the patient's chest wall, thereby increasing the functional residual capacity in underlying lung fields. As a result, increased ventilation and perfusion to the targeted internal lung field may be achieved by creating a decrease in the external barometric pressure relative to the more positive intrinsic airway pressures. The PXT device also may improve lung compliance by enabling a medical professional such as a Respiratory Therapist/Care provider to grab and elevate the chest wall to compensate for the dysfunction of the respiratory musculature responsible for lifting the chest wall during normal breathing, as described below. In some embodiments, once a targeted functional residual capacity (FRC) has been established, percussion may be applied with increased effectiveness due to greater oscillatory movement of chest wall, as described below.

The overall shape of the device 100 may mimic the size and shape of the human lung. For example, the outer shell 120 may forming a support structure for housing an arched hollow chamber (such as positive pressure chamber 150). This chamber 150 may interface with a membrane 130 that may cover and protect the patient's skin.

The shell 120 may be made of plastic and may be shaped similar to the human lung. Like the lung, it may have three segments: an apex segment, a medial segment, and a lower segment. Similarly, there also may be three main pressure points on the skin when the PXT device is in use. For example, the first pressure point may be at or above and resting on the trapezius muscle, the second pressure point may be lateral to sternum on ribcage, and the third pressure point also may rest on the patient's lateral rib cage, closer to the back posterior side of chest wall. More or less pressure points may be used, and the pressure points may be aligned with other parts of the patient's body. In some embodiments, the medial and lower segments may be combined and also referred to herein as the lower segment.

Depending on the design of the shell 120 and/or the membrane 130, pressure may be distributed evenly among the segments. Alternatively, or additionally, different pressures may be distributed to one or more segments, and different pressures may be distributed at each segment.

In some embodiments, some or all of the rest of the edges of the shell (i.e. other than at these three pressure points) may be recessed so that the three pressure points may absorb the most force when negative pressure is applied to chest. As a result, the patient's ribcage may be lifted until the recessed edges make contact with the ribcage. At this stage, the patient's chest may be lifted. Based on shape of the chamber, the chest may be lifted until the channels or slots of the membrane are in a desired position to treat the targeted area of lung. The medical professional then may lift the chest wall in desired directions, thereby improving chest wall compliance and reducing extrinsic airway resistance in hard to ventilate conditions like Respiratory Distress Syndrome (RDS).

In some embodiment, the shell 120 includes three, interconnected chambers 150. Interconnected chambers 150 may enable the medical professional to contour the PXT for a range of chest wall shapes, in order to treat patients with conditions such as scoliosis, kyphosis and the like.

Figure 2A:
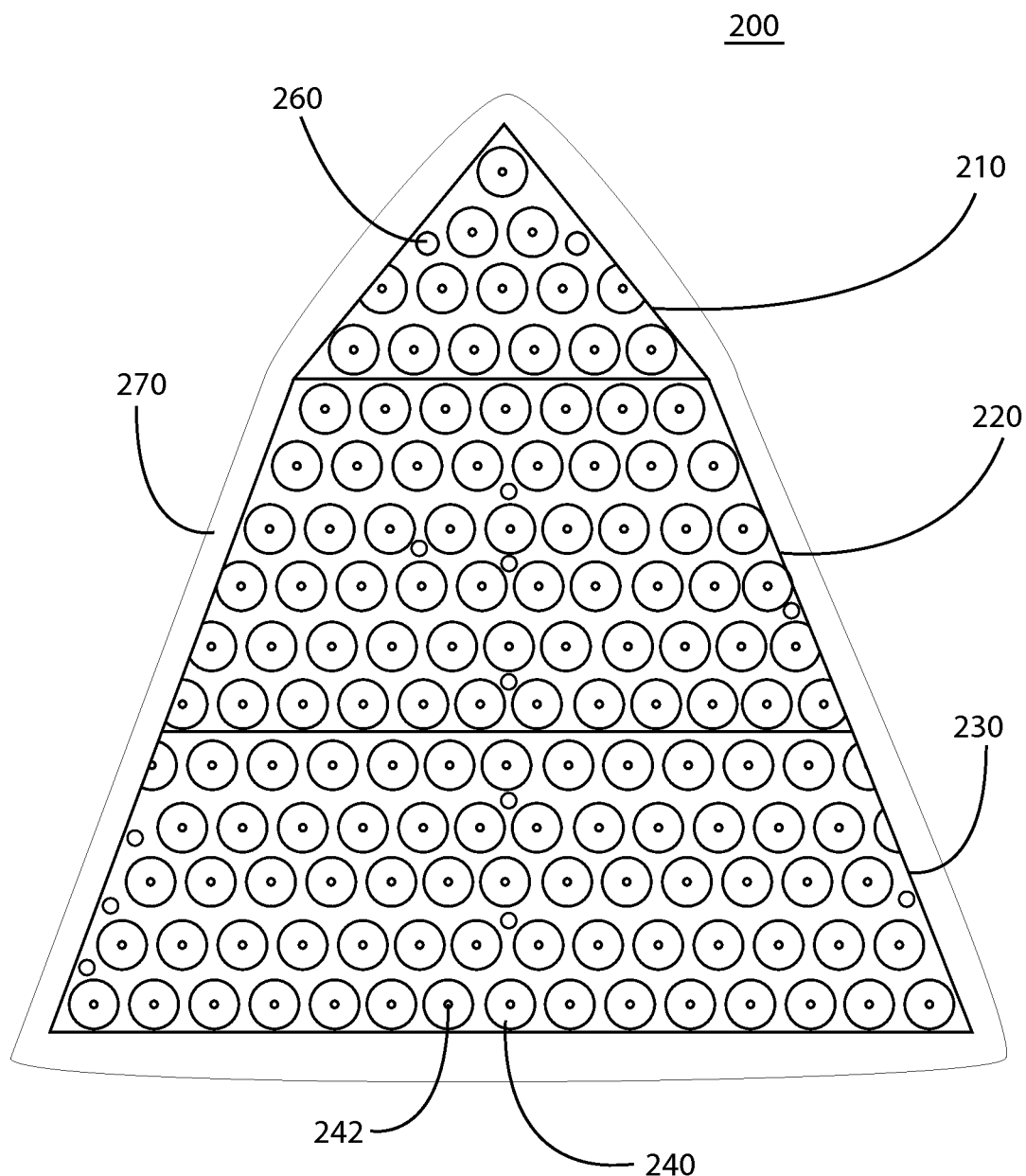
FIGS. 2a and 2b show a plan view of an exemplary membrane for use in a PXT device and a side view of a portion of an exemplary membrane for use in a PXT device, respectively.
Figure 2B:
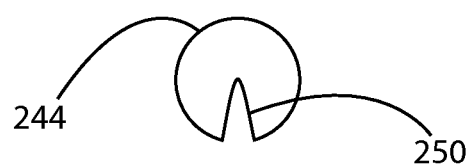

An exemplary membrane 200 is shown in FIG. 2. The membrane 200 may be made of a silicone elastomeric gel and also may have a thickness between about 0.2 centimeters (cm) and about 8 cm, preferably between about 1 cm and about 5 cm, and even more preferably between about 2 cm and about 3 cm. Other sizes also may be used.

In some embodiments, the membrane 200 may have a generally triangular shape to contour with the chest wall. Other shapes may be used. The skin side of the membrane 200 may have an overall concave shape, similar to that of a suction cup. The membrane may have three segments, an apex segment 210, a middle segment 220, and a lower segment 230. Each segment 210, 220 and 230 may have its own shape and/or dimensions. For example, an apex segment 210 may be substantially triangular and have a gently concave shape relative to the patient's chest. In some embodiments, each segment 210, 220 and 230 may have a concave shape.

The skin side surface of each segment may be further dimpled by concave suction cups 240. The suction cups 240 may have a circumference between about 0.1 cm and about 2.5 cm, preferably between about 0.5 cm and about 1.75 cm, and even more preferably between about 0.75 cm and 1.25 cm. One or more of the suction cups may provide airflow into a channel for air to escape (i.e. be sucked out into the negative pressure chamber 140) via one or more apertures 242. In the illustrated embodiment, an aperture 242 may be placed in the center of each suction cup 240.

Upon activation of PXT, the membrane 200 may become adhered to the patient's skin, thereby lending support and protection to the skin by forming a barrier that the skin cannot exceed. In some embodiments, these suction cups 240 may be filled with moleskin type material to form a contiguous, essentially flat concave surface to further protect and support the skin.

The interior side (opposite of skin side) of the membrane may be coupled to one or more air channels 244 that may protrude through the surface of the membrane and couple to the negative pressure channels 140. In some embodiments, a bicuspid valve 250 may be provided near the proximal end of the air channel 244. The bicuspid valve 250 may provide one-way flow through the channel 244 to assist in maintaining a net negative pressure on skin side of membrane 200. In addition, the bicuspid valve 250 also may able to generate measured bursts of positive pressures in the interior chamber 150, thereby oscillating the membrane and chest wall. This oscillation may be more effectively than current forms of chest wall manipulation because, as the skin side is net negative, the PXT device 100 adheres to the chest enabling the medical profession to grab and lift or otherwise manipulate the chest wall as desired. In this manner, the care provider may lift the membrane 200 in multiple directions to mimic respiratory musculature, thereby moving the chest wall in order to focus therapy to specific lung fields.

In addition, release valves 260 may be fitted onto the skin side of membrane 200 to disengage the membrane 200 from the patient. For example, the release valves may be operatively coupled to a positive pressure gas source 105 to form a quick release aperture that can evaluate skin integrity at any time during treatment. Reactivation may be triggered by pushing a button (see, for example, FIG. 7) to reactive negative pressure when the membrane 200 is in contact with the skin.

In some embodiments, the membrane 200 may be disposable, i.e. discarded after one or a small number of uses. In other embodiments, the membrane may be designed to withstand many uses, such as 100 uses, 1000 uses, 10,000 uses, or more.

In some embodiments, the surface area diameter of the portion of the suction cup 240 of the membrane 200 that attaches to a patient's chest may be smaller than diameter of cup 240. In such a case, the smaller surface area occupied by the cup 240 may allow for greater contraction of the membrane 200 during tail wagging motion (described below). Thus, rather than having the membrane 200 dimpled with recessed concave cups 240, the cups 240 may be somewhat external to the membrane 200, where the connection to the membrane 200 may be slightly larger than the lumen 140 opening 242 in center of cup 240, similar to that of an octopus' tentacle. This may allow for greater stretching motion, like webbing between the percussion diaphragms (described below).

The membrane 200 and/or shell 120 may be custom shaped to an individual patient. To determine the appropriate shape of a given patient, the patient's chest wall may be measured. Next, the distance from the manubrum of the patient's clavicle medial to acromion process may be measured used to determine a size of the bottom width of apex chamber. For example, the bottom width of the apex chamber may be about the same size as this distance. The pressure point for the apex may be aligned to rest on the trapezius muscle, and the recessed supports of the lower width of apex chamber may be aligned to come to rest on the patient's clavicle close to end where clavicle meets the manubrum, and medial to acromion process.

By using clavicle as landmark, a medical progression may be able to enhance lung expansion in lung apeces by lifting the clavicle, effectively suspending a patient through negative pressure field generated over lungs. Manual movement of the patient's shoulder also may be used in conjunction with PXT device manipulation to further enhance lung expansion.

Currently, medical professional may suture the clavicles in order to suspend patient, such as children, by their clavicles to effect chest wall compliance. Employing the principles described above, a medical professional may utilize a PXT device to achieve the same goal in a non-invasive manner, improving ventilation of patients as well as perfusion of specific lung fields. In addition, the patient may be placed in various prone positions to apply PXT treatment to any or all lung fields, anterior or posterior, to facilitate and enhance perfusion.

Figure 3A:
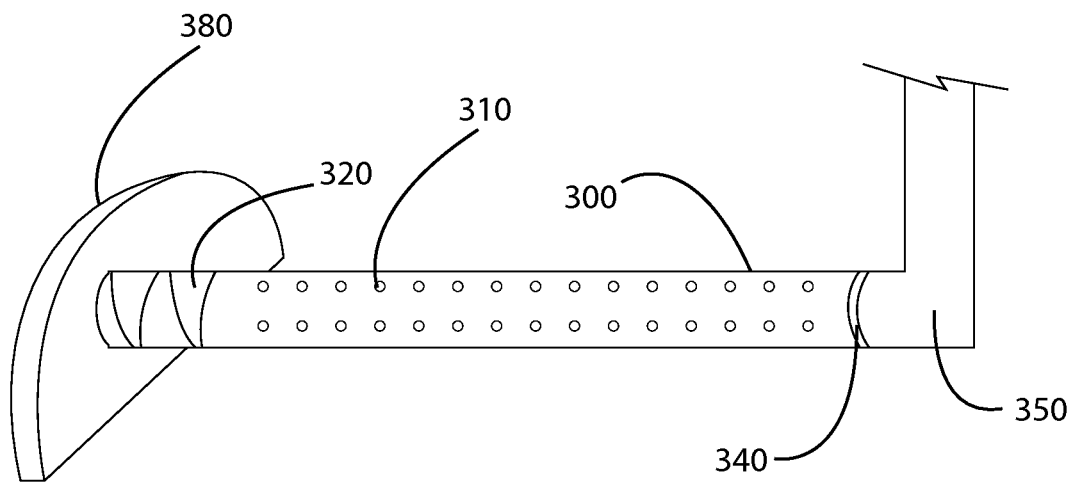
FIGS. 3A-B show exemplary inflow tubes for use in a PXT device.
Figure 3B:
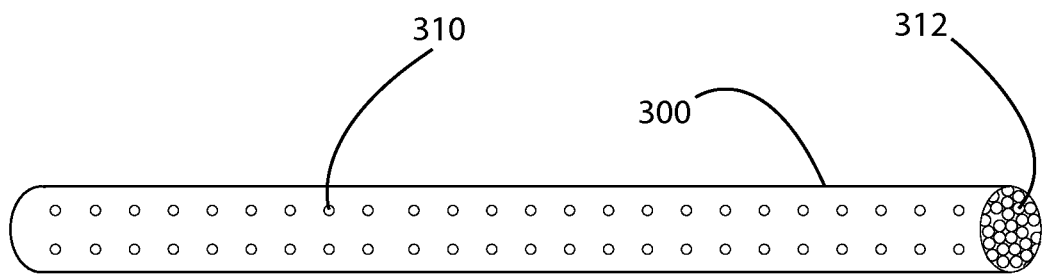

Exemplary inflow tubes 110 are shown in FIGS. 3A and 3B. In FIG. 3A, an exemplary inflow tube 300 is shown attached to a connector segment 350 via a rotatable joint 340. The connector segment may couple the inflow tube 300 to a device handle 170. The inflow tube 300 may also be coupled to a divider block 3580 and include angled divisions 320 to enable movement of the tube 300 as the handle 170 is rotated to provide dynamic contouring of the membrane 130, as described above.

The inflow tube 300 may include a plurality of outlets 310 that provide passages for air inflow into the one or more positive pressure chambers 150. Each outlet 310 may provide airflow to a single corresponding passage 150 or multiple 310 outlets may provide airflow to the same passage 150. In the embodiment of FIG. 3A, the inflow tube 300 may provide the same airflow to each outlet 310.

In the embodiment illustrated in FIG. 3B, each outlet 310 may be coupled to a corresponding pressure tube 312 that provides airflow to a single corresponding passage 150. As a result, each chamber 150 may be individually pressurized. Individual pressurization may enable various modes of operation, such as oscillatory patterns like wave patterns, shiatsu or the like, to be provided, either on demand by the medical professional or via a predetermined program. Other modes of operation, such as those described herein, also may be provided.

An exemplary divider block 380 may provide various functions in the overall use of the PCT device 100. First, the divider block 380 may separate the apex segment from the medial segment and/or lower segment to assist in alignment of the PCT device on the patient. For example, the operator may align the divider block 380 on or near a patient's clavicle to properly align the PXT device. The divider block 380 may provide a structure that receives the inflow tube 310, allowing it to rotate or the like. In the illustrated embodiment, the inflow tube 310 may be fenestrated to allow for rotation and/or contortion of the membrane. The divider block 380 also may provide a channel for airflow from the negative pressure chambers to the outflow tube. The divider block 380 also may allow the operator to direct and/or control the angle of chest lift. For example, as the divider block 380 is the base of the ball and swivel (see FIGS. 7-14 and accompanying description below), the angle of the divider block 380 may determine the amount of arch of the spine (inflow tube 310) when contouring to chest wall. As such, the positioning of the divider block 380 may allow for targeting specific lung fields.

The overall size of the PXT device 100 may vary depending on the size of the patient's chest and/or lung. For example, a divider block 380 may be about the size of the patient's clavicle. Thus, for a typical neonatal patient, the divider block 380 may have a width between about 2 centimeters (cm) and about 4 cm and preferably about 3 cm. Similarly, for a typical pediatric patient, a divider block may have a width between about 3 cm and about 7 cm, preferably between about 4 cm and about 6 cm. Finally, for a typical adult patient, a divider block 380 may have a width between about 6 cm and about 12 cm, preferably between about 7 cm and about 10 cm.

The sizes of the apex and lower segments may be based on the size of the divider block. For example, the apex may form a triangle having a height between about the half the size and about twice the size as the width of the divider block, and preferably about the same size as the width of the divider block. Similarly, the height of the lower segment may be between about the same size as the width of the divider block and about three times the width of the divider block, preferably between about one-and-a-half times the width of the divider block and about two-and-a-half the width of the divider block, and even more preferably about twice as long as the width of the divider block. In one example of a device for a neonatal patient, the divider block may be about 3 cm wide, a triangularly shaped apex may have a height of about 3 cm, and a trapezoidal lower segment may have a height of about 6 cm. Other shapes and sizes may be used for the divider block, apex, and lower segments.

Figure 4:
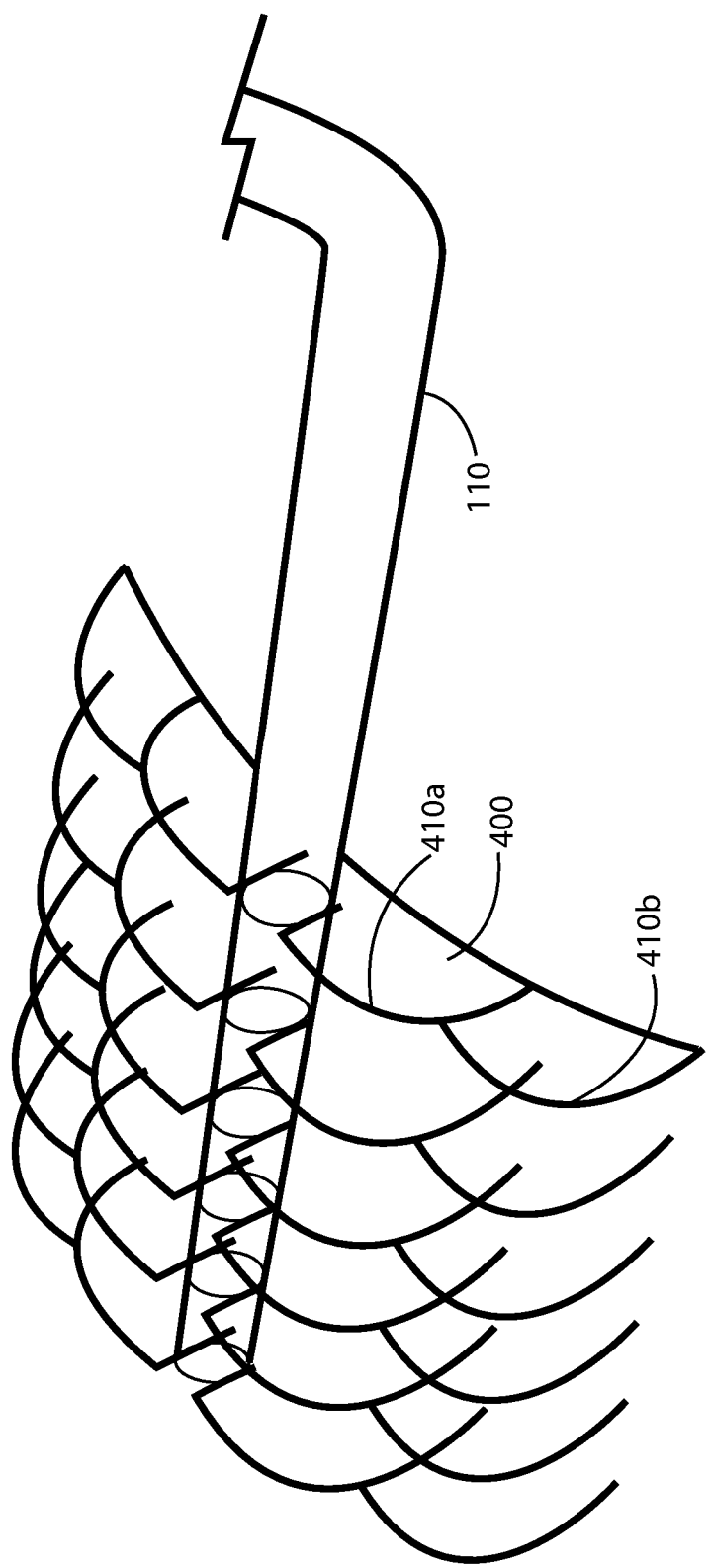
FIG. 4 shows an exemplary configuration of negative pressure lumens for use in a PXT device.

Referring to FIG. 4, an exemplary configuration 400 of negative pressure lumens 140 are shown. In the illustrated embodiment, various negative pressure lumens 140 provide cantilever shaped ribs 410a and 410b that run from the apex segment through the medial segment and out the lower segment. Some negative pressure lumens 140 may act like a backbone 410a for the shell 120, and may form upper interior dome for positive pressure chamber 150. In some embodiment, the backbone lumens 410a may be shorter compared to the three pressure points. Each negative pressure lumen 140 may open to each suction cup for generation of negative field.

Each rib 410b may be able to rotate, such as for example, between about 60° and about 230° and preferably between about 90° and about 180°. The ribs 410a and 410b may then come to rest in a balanced manner onto the chest wall, thereby providing contourability to get a seal on misshapen chest walls. Each backbone 410a and adjoining rib 410b pair then rests on chest wall. The back pressure points are also cantilevered to form vertebrae 1 and the lower width of the shell. For example, the apex backbone might include twenty-four vertebrae, with 8 vertebrae for each segment. As noted above, the internal portion of vertebra is open to each vacuum chamber. Having control of axial rotation of each vertebral opening or fistula to control size of fistula could be used to, for example, manipulate chamber pressures relative to one another. Manipulation of negative pressure of individual chambers may further enhance PXT's ability to target specific lung areas, as well as to deactivate one chamber due to chest tubes, or indwelling catheters or surgery sites.

Figure 6:
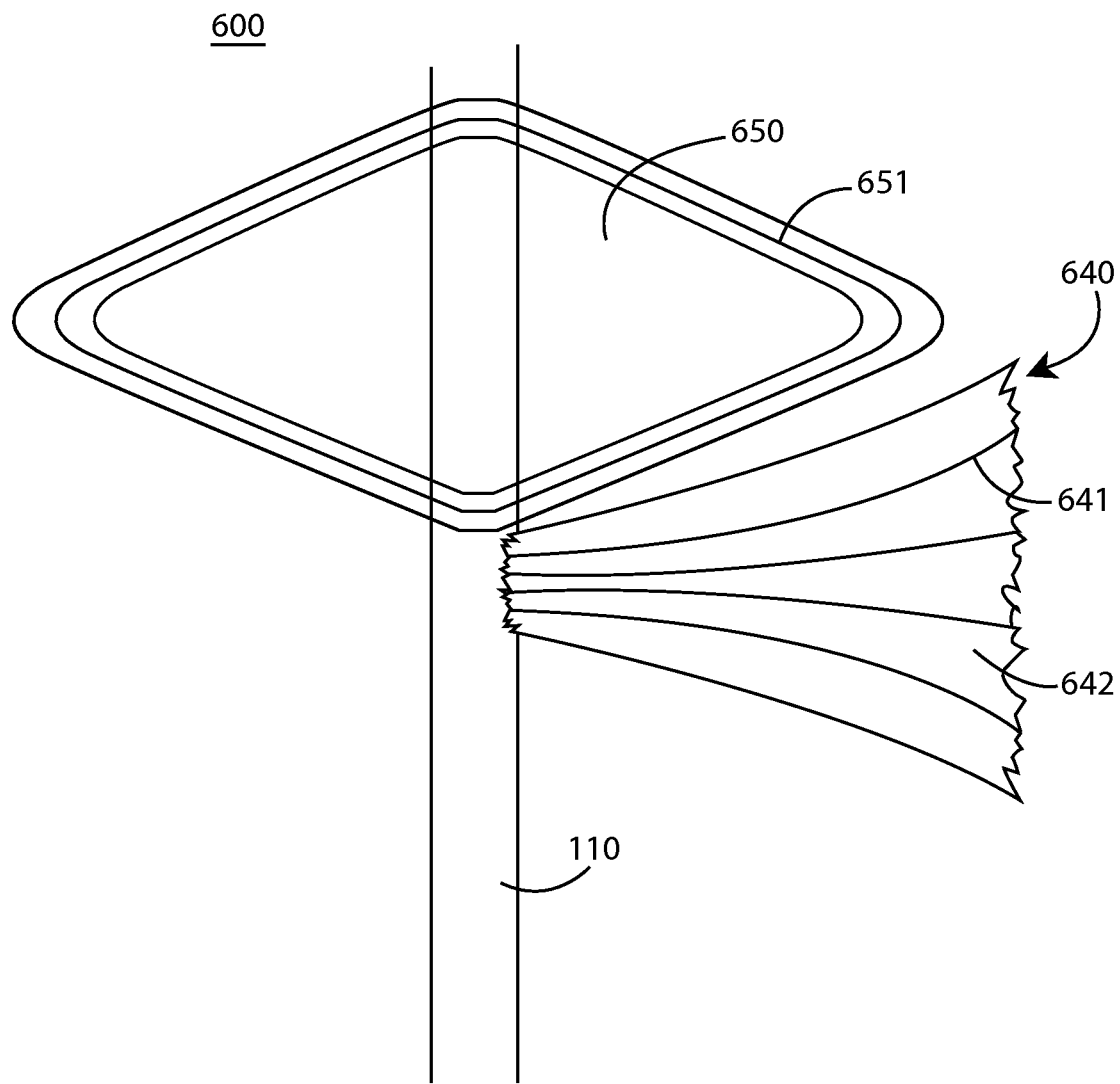
FIG. 6 shows a partial view of exemplary positive pressure chambers and negative pressure chambers in a PXT device.

FIG. 6 shows a partial view of exemplary positive pressure chambers and negative pressure chambers in a PXT device. In some embodiments, the positive pressure chamber 650 may cover the backbone 410a and ribs 410b, whose cantilevering arrangement form an arch or spherical exterior shape to the vacuum chamber segments with varying widths. The vacuum or negative pressure chambers 640 may be defined by a negative pressure chamber membranes 642 that, for example, drape over the backbone 410a and ribs 410b. The positive pressure chambers 650 also may include percussion diaphragms that may interface with the outer shell 120. The airflow source 105 may be may be connected to a diaphragm that is superior to a vacuum chamber, and overlaps, but is still smaller than vacuum chamber. This arrangement where the diaphragm rests on the external side of vacuum chamber, allows percussion to effect all three segments of chamber in concert and/or in synchrony. The bursts of pressure may oscillate the chest wall. Both the frequency and the amplitude of these oscillations may monitored and/or adjusted based on patient size and tolerance. Both the positive pressure chambers 650 and negative pressure chambers 640 may include pleats 651 and 641, respectively, or other similar features to allow for expansion and contraction as the pressures within the chambers 650 and 640 varies. Exemplary embodiments showing percussive diaphragms are shown in FIGS. 7-15.

In addition, the negative pressures in the negative pressure lumens 140 and/or negative pressure chambers 640 may be monitored and/or adjusted, as may the pressures the between membrane and the skin. For example, a regulator may be provided to control and/or adjust the negative pressures in the negative pressure chambers to reach desired levels. Pressure levels may be output in PSI, millimeter of mercury (mmHg) or the like.

Figure 5:
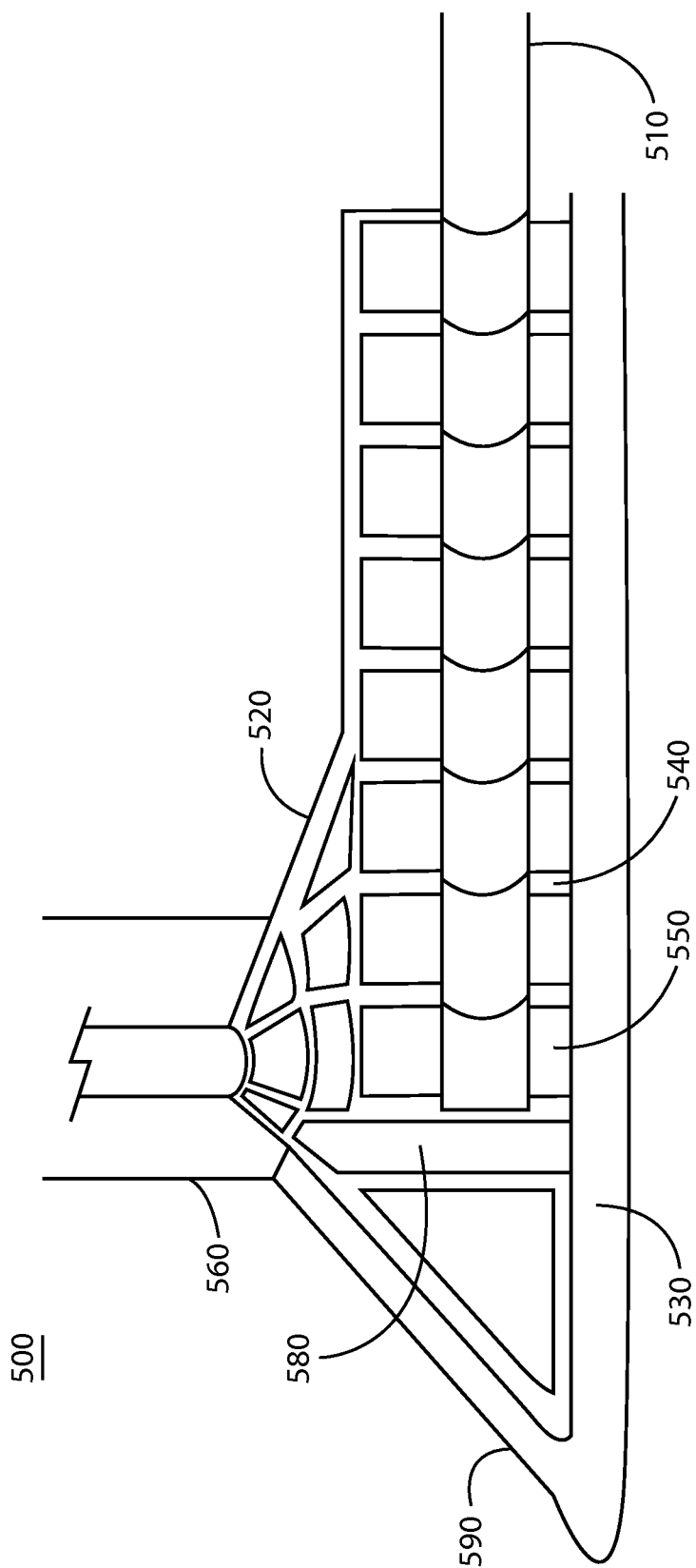
FIG. 5 shows a perspective view another exemplary pulmonary expansion therapy (PXT) device.

Another exemplary PXT device 500 is shown in FIG. 5. In the illustrated embodiment, the device 500 includes an inflow tube 510, connected to divider block 580 housed in a shell 520. The shell 520 may also house a plurality of positive pressure chambers 550 and negative pressure lumens 540, which may be operatively coupled to suction cups on a membrane 530.

In the illustrated embodiment, the lumens 540 may form into semi-rigid rubber tubes that may attach to negative pressure source 105. The lumens may be between about 0.3 cm and about 10 cm, preferably between about 2 cm and about 7 cm and even more preferably between about 3 cm and about 5 cm.

Columns defined by the positive pressure chambers 550 and/or the negative pressure lumens 540 may be evenly spaced. The positive pressure chambers 550 may be collapsible/inflatable, depending on the desired negative pressure to grab chest wall. In the illustrated embodiment, each positive pressure chamber 550 is individually addressable. In other words, the pressure in each positive pressure chamber 550 may be modified individually because airflow to each chamber may be modified individually, such as for example, via a specific pressure tube (312 in FIG. 3) coupled to the chamber 550. These chambers 550 also may be oscillated at various pressures and frequencies, such as, for example, after grab is achieved. The chamber 550 may be oscillated in unison and/or may have various rhythmic patterns preset like that of a massage chair. Depending on the length/depth of the suction cups, the pressure chambers may be positioned near or in contact with membrane 530 and/or the patient's skin. This may enable more effective chest wall manipulation for airway clearance.

In addition, the device 500 may also include a front support 580 that provides support for the shell 520. The front support 590 may have a variable geometry to allow the device 500 to achieve increased contourability of the patient's chest. For example the front support shell may be telescoping to contract and/or expand as necessary. Alternatively, or additionally, the front support 590 may be made of a flexible plastic material that allows may contract and/or expand in size. Other materials and/or methods may be used to provide a variable geometry front support 590.

Figure 7:
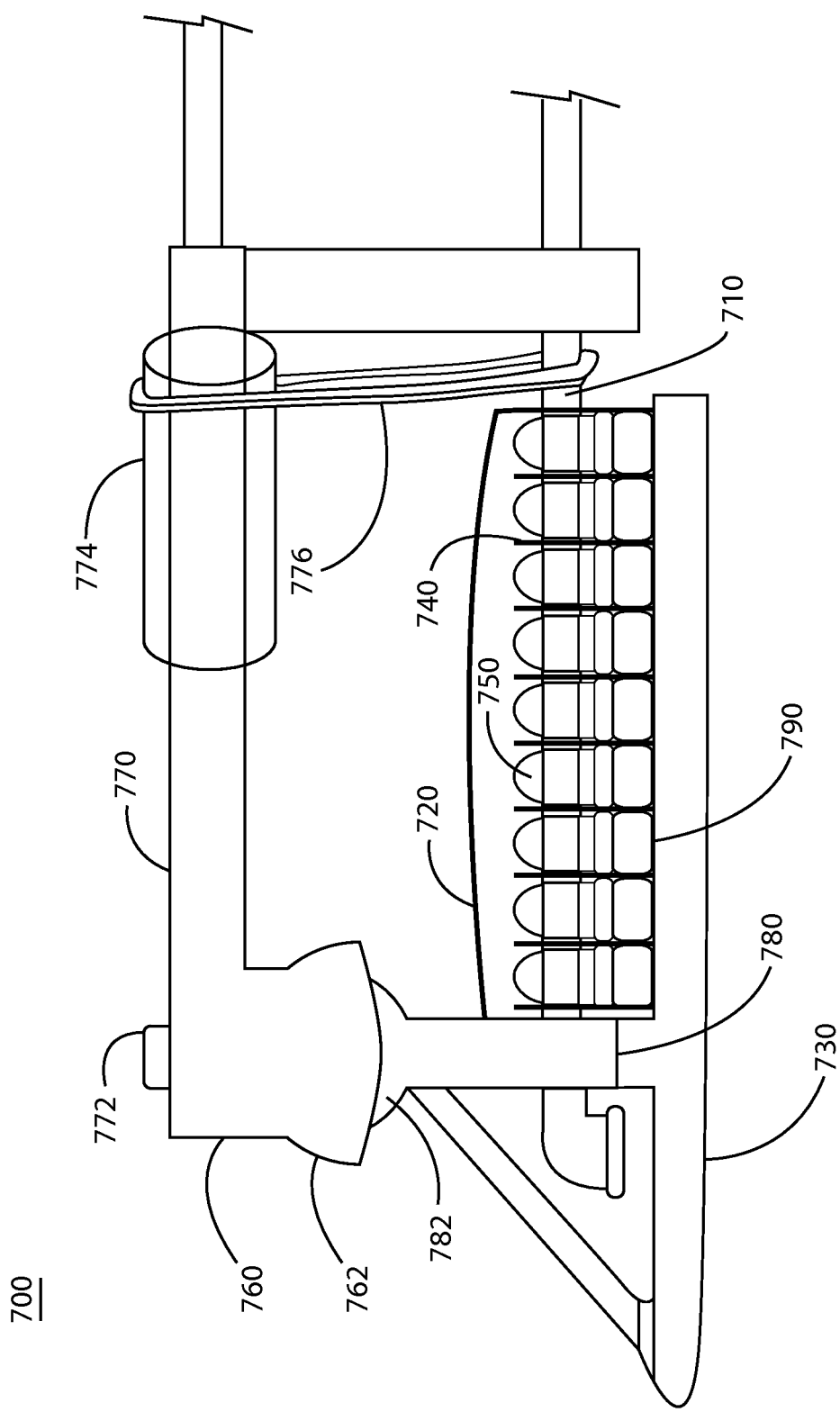
FIG. 7 shows a perspective view of another exemplary PXT device.

FIG. 7 shows a side view of another exemplary PXT device 700. In the illustrated embodiment, the PXT device 700 may include an inflow tube 710, an outer shell 720, a membrane 730, one or more negative pressure chambers 740, one or more positive pressure chambers 750, an outflow tube 760, a handle 770 and a divider block 780. The PXT device 700 also may include one or more percussive diaphragms 790, a pressure release button 772 and a contour sleeve 774 operatively connected to the inflow tube 710 by a cable 776. The divider block 780 may include a ball 782 that engages a socket 762 to enable rotation of the device 700 and/or contortion of the membrane 730.

The ball joint 782 may enable targeted angling of the divider block 780. With targeted angling of the divider block 780, an operator may apply an upward force to either (1) lift upward as when lifting the clavicle or (2) pull chest outward by positioning the divider block 780 at about 90° to the chest, for example, when targeting the lower lobes at the lateral lower lobes. The ball joint 782 swivel also may allow for the spine or to be arched upward like a cat stretching. This contour will be beneficial when targeting the lower lobes by wrapping around lateral lower chest wall.

The length of the spinal column (inflow tube 710 and negative pressure lumens 740) may affect the amount of arch produced by the spine when the apex chamber and the divider block 780 are pointed downward.

The sleeve 774 may act as a control mechanism for twisting the spine. For example, the spine may be rotated by rotating the sleeve 774 over the handle 770, similar to an accelerator on a motorcycle handle bar. Because the cable 776 is operatively connected to the sleeve (e.g. wrapped around the sleeve 774) and connected to the inflow tube, rotation of the spine may mirror the rotation of the sleeve 774. Alternatively, or additionally, various mechanisms (not shown) may be used to alter the ratio of rotation of the sleeve 774 to rotation of the inflow tube 710.

The ball 782 and socket 762 interface between the divider block 780 and the outflow tube 760 may allow for greater flexibility and/or contortion of the PXT device 700, as well as strength and support. For example, when lifting the device 700 by applying an upward force on the handle 770, thereby lifting the patient's chest, the operator may be able to dynamically adjust the angle of the force to target specific lobes of the patient's chest.

In some embodiment, a similar ball and socket interface may be provided between the divider block 780 and the inflow tube 710. This arrangement may provide increased flexibility of the device 700 as an assemblage of individual segments; either the percussive chamber vertebrae, the ribcage vertebrae, or cushioned rubber spacers that form a sealed spinal column. The improved flexibility of the spine, and because of the ball and socket interfaces, the inflow tube may form an arc shape when contorted. As the middle of the spine is raised relative to divider block, the device also may better contour to the patient's lower lobes (when holding device in horizontal position).

Figure 8:
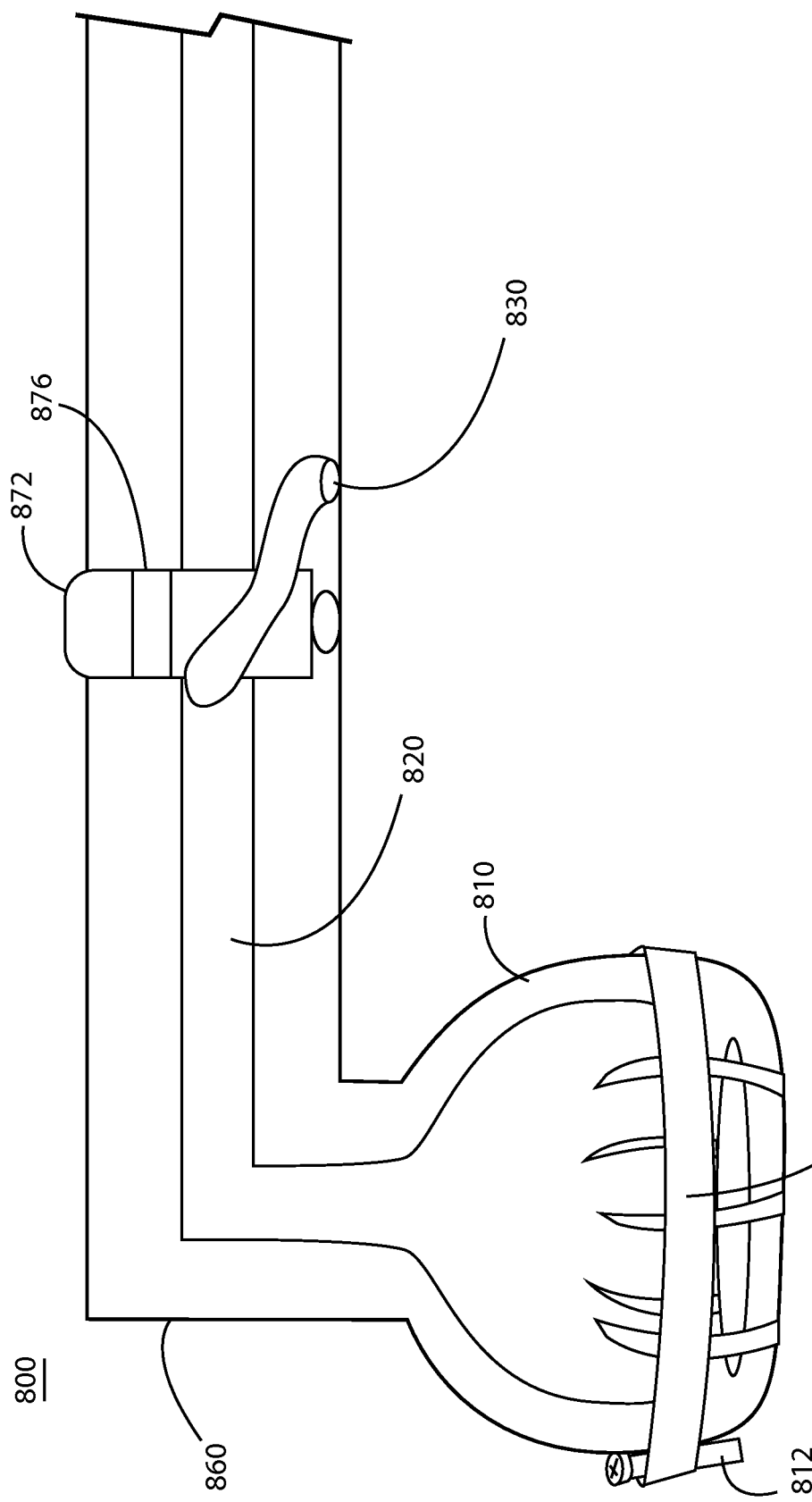
FIG. 8 shows a cutaway of a portion of the exemplary PXT device of FIG. 7.
Figure 9:
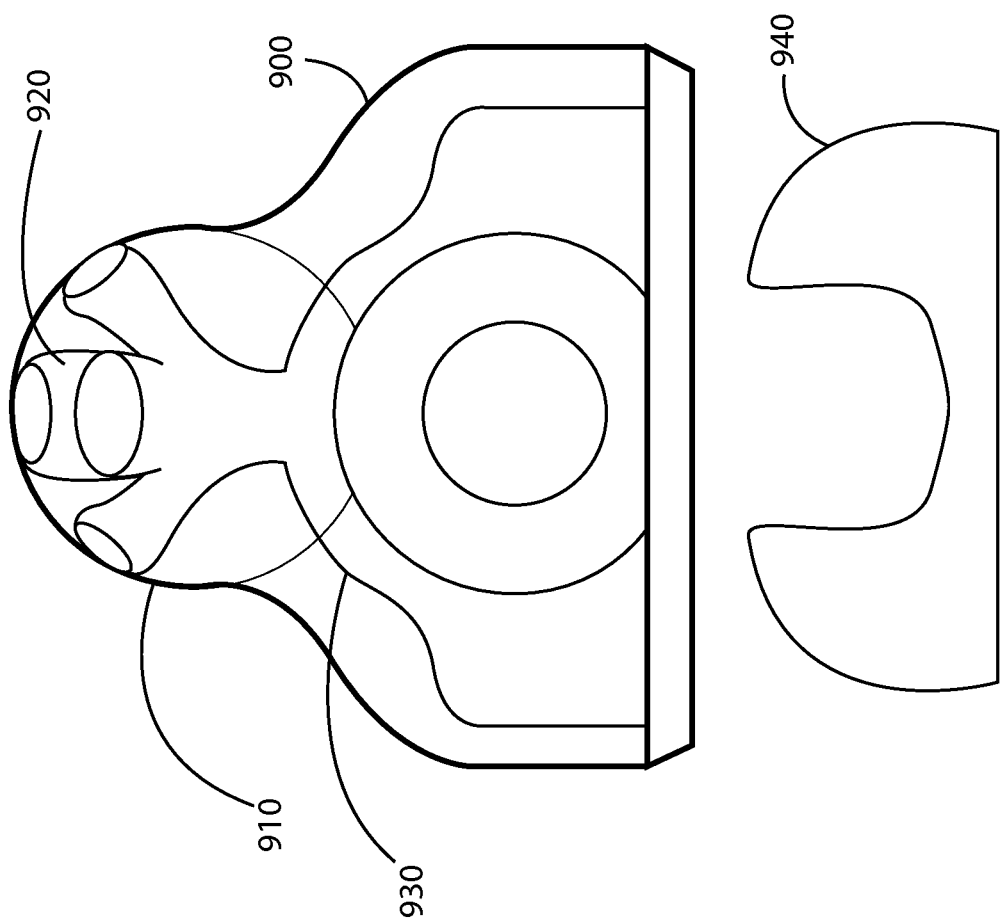
FIG. 9 shows a partial view of a portion of the divider block of the exemplary PXT device of FIG. 7 with a portion of an exemplary membrane.

FIGS. 8 and 9 show additional aspects of the ball and socket interface between the divider block 780 and the outflow tube 760. A positive pressure column (PPC) may be connected to the handle, preferably at a 90° angle relative to the handle. The PPC at the top may have a sleeve (PPCS) over the handle, as shown in FIG. 7. The PPC and PPCS may be fixed at a 90° angle onto the handle and may run parallel to 90° angle of the handle socket above the divider block 780.

As shown in FIG. 8, the mechanism of control of vacuum/negative pressure is shown. A button 872 may be located on the handle, such as at or near the 90° bend above the divider block. The button may also be located at other positions on the handle. When the button 872 is depressed, a negative pressure source may be activated and transferred, negatively pressurizing desired features of PXT. This may be achieved, for example, by providing an aperture 876 in the column of the button mechanism 872 that, when depressed lines up with a channel 820 in the outflow tube 860 and thereby a negative pressure source. Other mechanisms to operatively couple the negative pressure source with the negative pressure chambers also may be used. In some embodiments, a locking mechanism (not shown) may be incorporated to allow an operator to toggle between an 'on' mode in which the negative pressure source is operatively connected to the negative pressure chambers and an 'off' mode in which the negative pressure source is disconnected from the negative pressure chambers. Alternatively, or additionally, an operator may be required to hold down the button 872 in order to keep the negative pressure source operatively coupled to the negative pressure chambers.

In some embodiments, the button 872 may be positioned over a spring that allows for button to be at rest in up position. The inside of the button column also may include an open port that allows for the introduction of ambient air at barometric pressure. If a situation arises in which the therapy needs to be discontinued, the operator may disengage the negative pressure source by returning the button to the up (or disengaged or 'off') position. In response, the chest wall may be released by the device 700.

In some embodiments, a clamp 812 and band 814 or similar mechanism may be used to removably attach the socket 810 of the handle 770 to balls 910 of devices of various sizes. In this manner, the same handle 770 may be used to treat neonatal patients, pediatric patients, or adult patients. Alternatively, a handle 800 may be non-removably attached to the divider block 900 of a particular device 700. In either case, the strength of the ball and socket joint may be important, as the upward force generated by a Respiratory Care Practitioner (RCP) by lifting upward is transferred to chest wall through this interface. In some embodiments, the outflow tube 760 may for a substantially right angle with the handle 770 to provide for increased strength and directability. Other angles may also be formed between the outflow tube 760 and the handle 770, such as angles between about 60° and about 120°.

The ball 910 of the divider block 900 may include a plurality of lumens 920 or chambers that allow for transfer of negative pressure through the divider block 900 to the negative pressure chambers 740 in the lower segment of the device 700. In some embodiments, the divider block 900 may include a hollow portion 930 having a height that allows for the membrane 940 to be pulled up into this interior slot 930 when negative pressure is applied, thereby lifting the clavicle the same length and angle.

Figure 10:
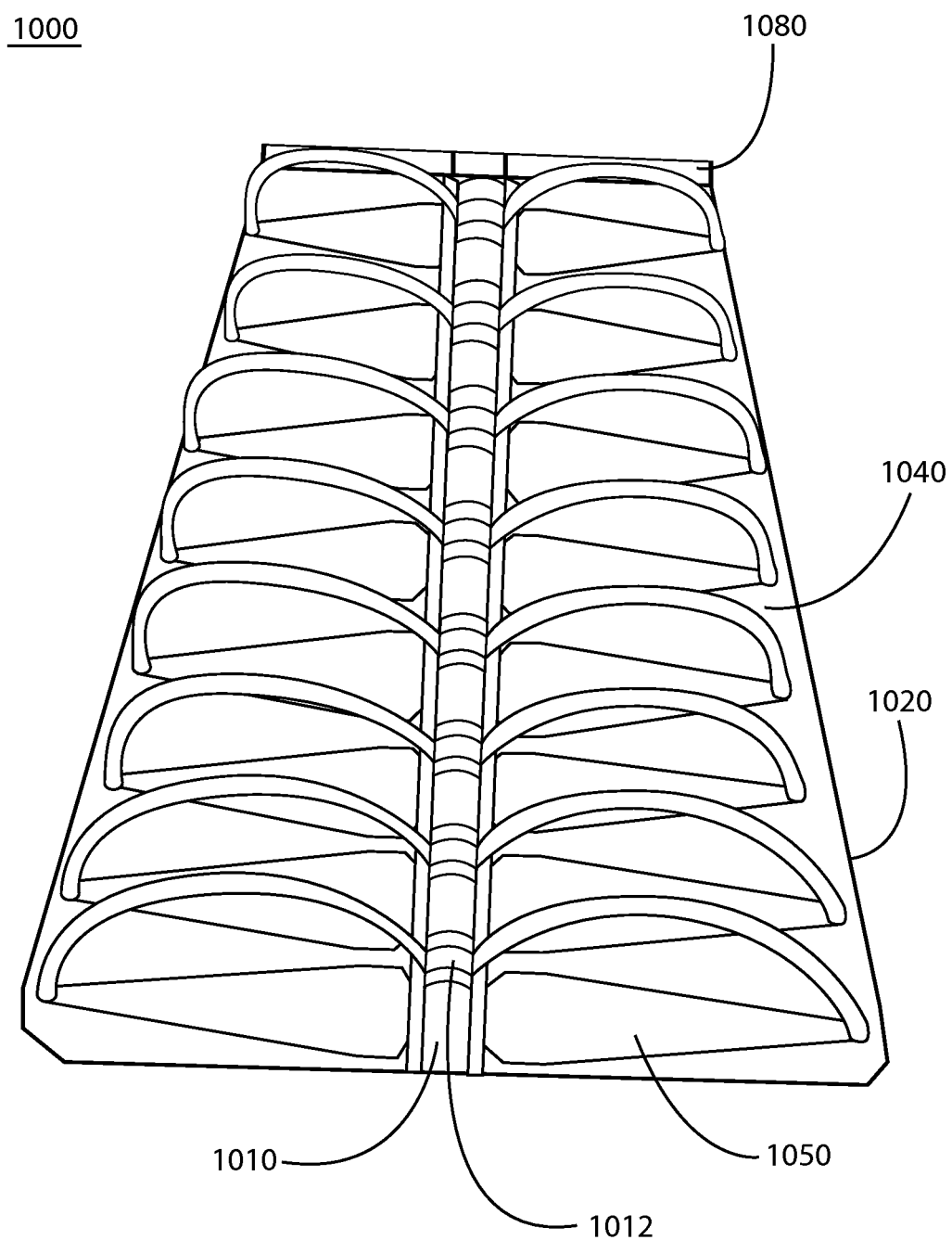
FIG. 10 shows a partial perspective view of the ribs and percussive diaphragms in the exemplary PXT device of FIG. 7.
Figure 11:
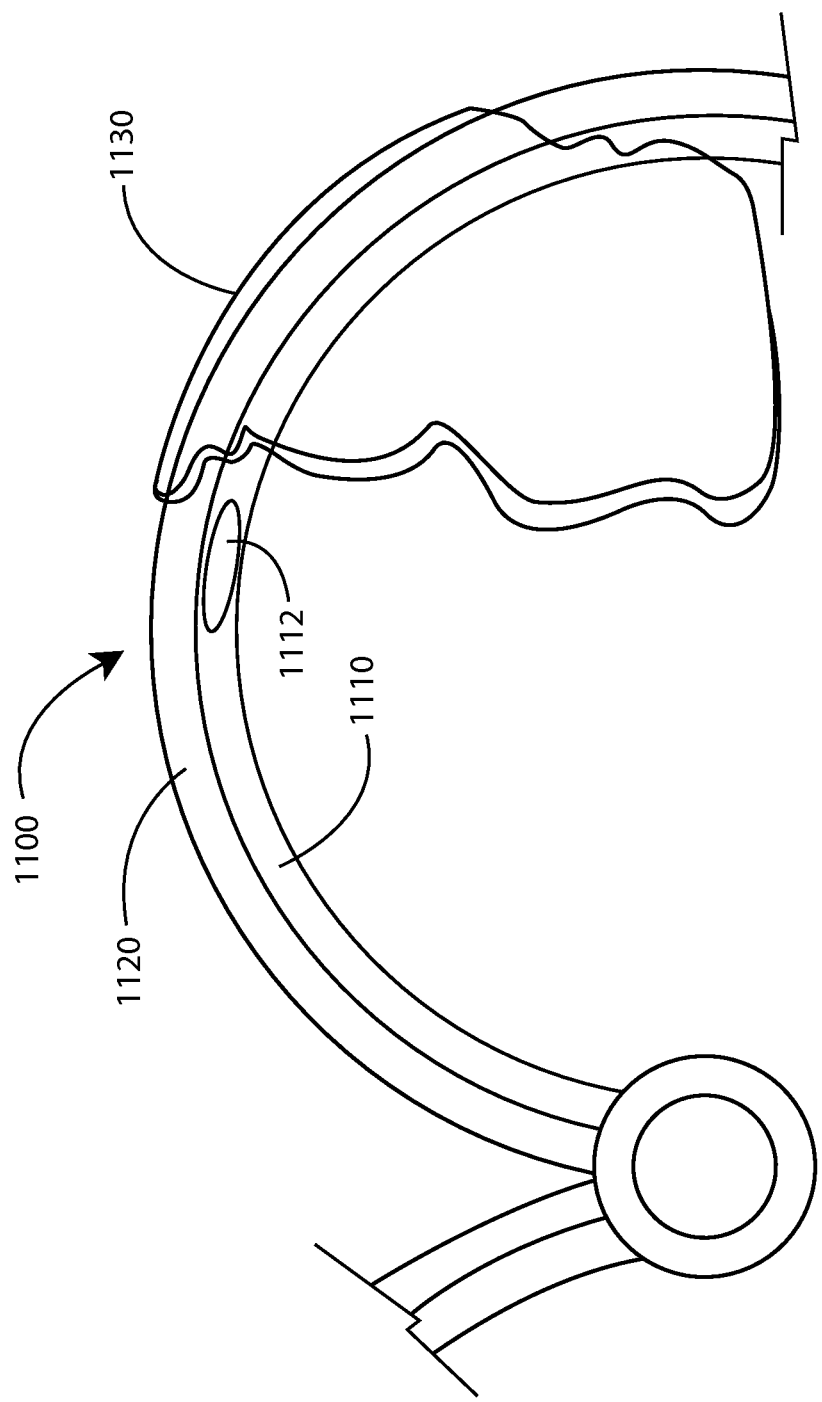
FIG. 11 shows a plan view of an exemplary double chambered rib of the exemplary PXT device of FIG. 7.

A portion of an exemplary lower segment 1000 is shown in FIG. 10. The lower segment 1000 may include a plurality of negative pressure lumens 1040 or ribs, and a plurality of positive pressure chambers that each include at least one percussive diaphragm 1050. The positive pressure chambers (also referred to herein as percussion chambers) may be individual chambers or shells that may be pressurized (or inflated) individually through outlets in the inflow tube 710, as discussed above. In some embodiments, the percussion chambers may be substantially diamond shaped. The use of a diamond shape may allow for the device 700 and membrane 730 to move laterally, as the divider block 780 and apex chamber 735 are the head, and spine and lower chambers can be thought of as a tail wagging side to side.

As an analogy to help conceptualize the device 700, the apex chamber 735 and divider block 780 may be considered the head and shoulders of the PXT device 700 while the inferior portions may be referred to as the body and/or tail. To continue the analogy and as noted above, the inflow tube 710 may be considered the spine while the negative pressure chambers 740 may be considered vertebrae. This configuration may allow for lateral movement like the wagging of the tail portion from side to side and the rotator sleeve 774 may allow for rotation of the spine to achieve greater contour to a patient's chest wall. In the embodiment illustrated in FIG. 10, the inflow tube 1010 may include cushioned spacers 1012 that act like discs in the human spine to allow for lateral movement.

In operation, as negative pressure is applied to the body/tail of a PXT device 700, negative pressure chambers 740 are formed within membranes 642 that are provided around the negative pressure vertebrae 740, which receive support from spine 710. This is shown, for example, in FIG. 11. As illustrated, the negative pressure lumens 1110 may be one of two channels or ribs (1110 and 1120) of a vertebrae 1100. An aperture 1112 may be provided, such as at the apex of the inferior rib 1110 to pressurize the negative pressure chambers 740 defined by negative pressure chamber membrane 1130 (shown partially), transferring negative pressure to the membrane 730 for adherence to the chest wall. The superior rib 1120 of the vertebrae may provide negative pressure to create the vacuum effect that enables the membrane/skin interface.

The ribs 1110 and 1120 of the vertebrae may be made of flexible material such as rubber or the like to allow for contortion of the device 700 during therapy. Other materials, such as metals or alloys may also be used. In some embodiments, the vertebrae may be fixedly attached to the spine (inflow tube 710). For example, notches may be provided in the spine to receive a corresponding portion of a vertebrae. Alternatively, some movement or rotation of the vertebrae 1110 and 1120 relative to the spine 710 may be allowed. The vertebrae 1110 and 1120 may be attached to one another, or may be separate from one another.

In operation, as the force generated by the negative pressure is directed toward the patient, and the positive pressure is generating force in the opposite direction, thereby percussing the chest wall, the ribcage (negative pressure chambers 740) would lie above the spinal column (inflow tube 710) thereby generating downward force to spine (inflow tube 710). Therefore, in some embodiments, the positive pressure chambers 750 may lie below the spine 710 to maximize transfer of force to chest wall without placing excess pressure on vertebral connection to tension bars (described below).

Figure 12:
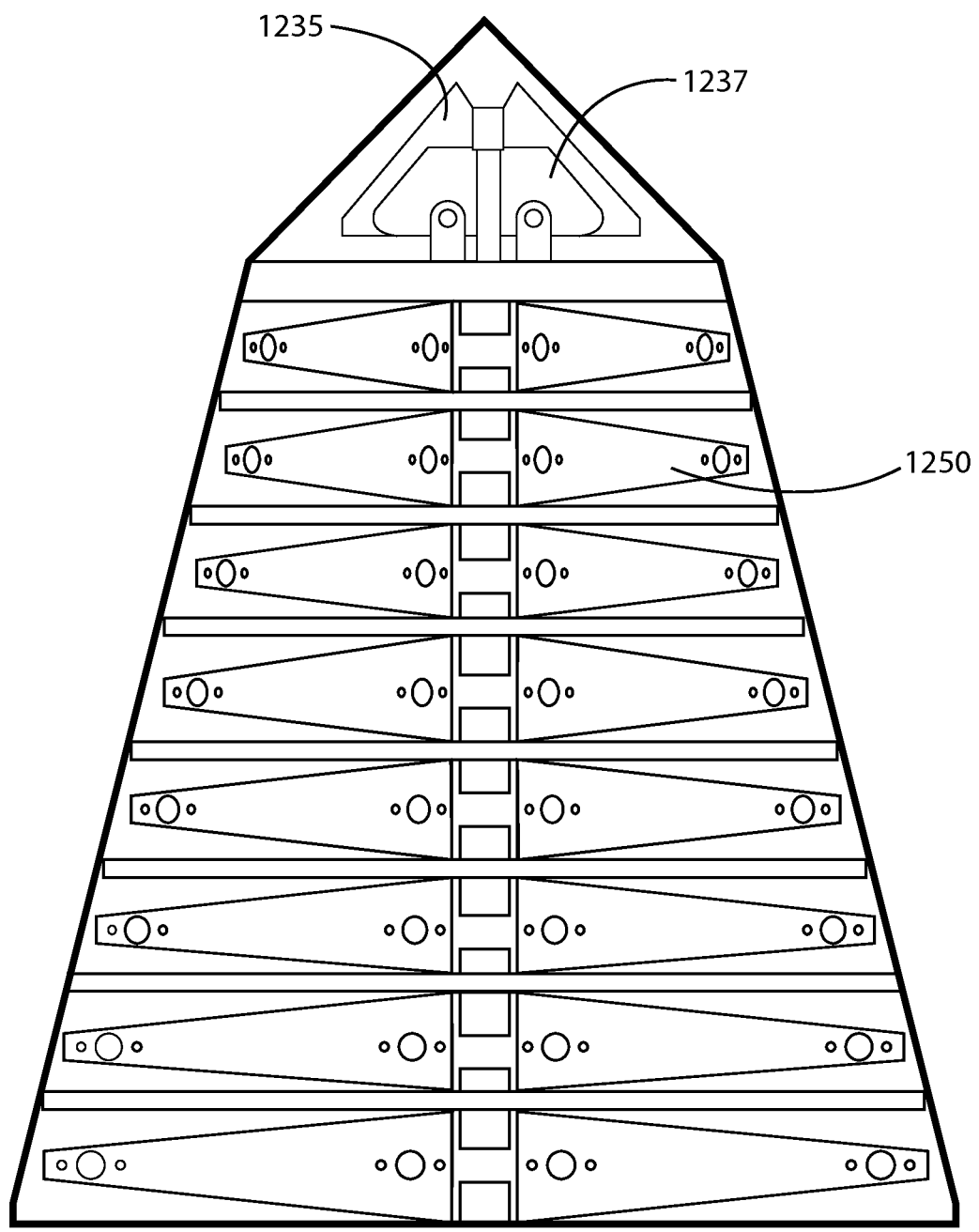
FIG. 12 shows a top view of a portion of the exemplary PXT device of FIG. 7.

FIG. 12 shows a top view of a portion of a PXT device 1200. In the illustrated embodiment, the lower segment include a series of chamber rows, each row having two positive pressure percussion chambers 1250. In addition, the apex segment 1235 also includes a percussion chamber 1237.

As noted above, the ability to lift the chest wall of a patient may be considered the primary function of the PXT device 700. Once desired expansion of lung volume, or Functional Residual Capacity (FRC) is achieved, the operator may then initiate percussion therapy in order to dislodge any mucous plugs or the like that may potentially be the cause of an obstruction in the patient's airways.

Figure 13:
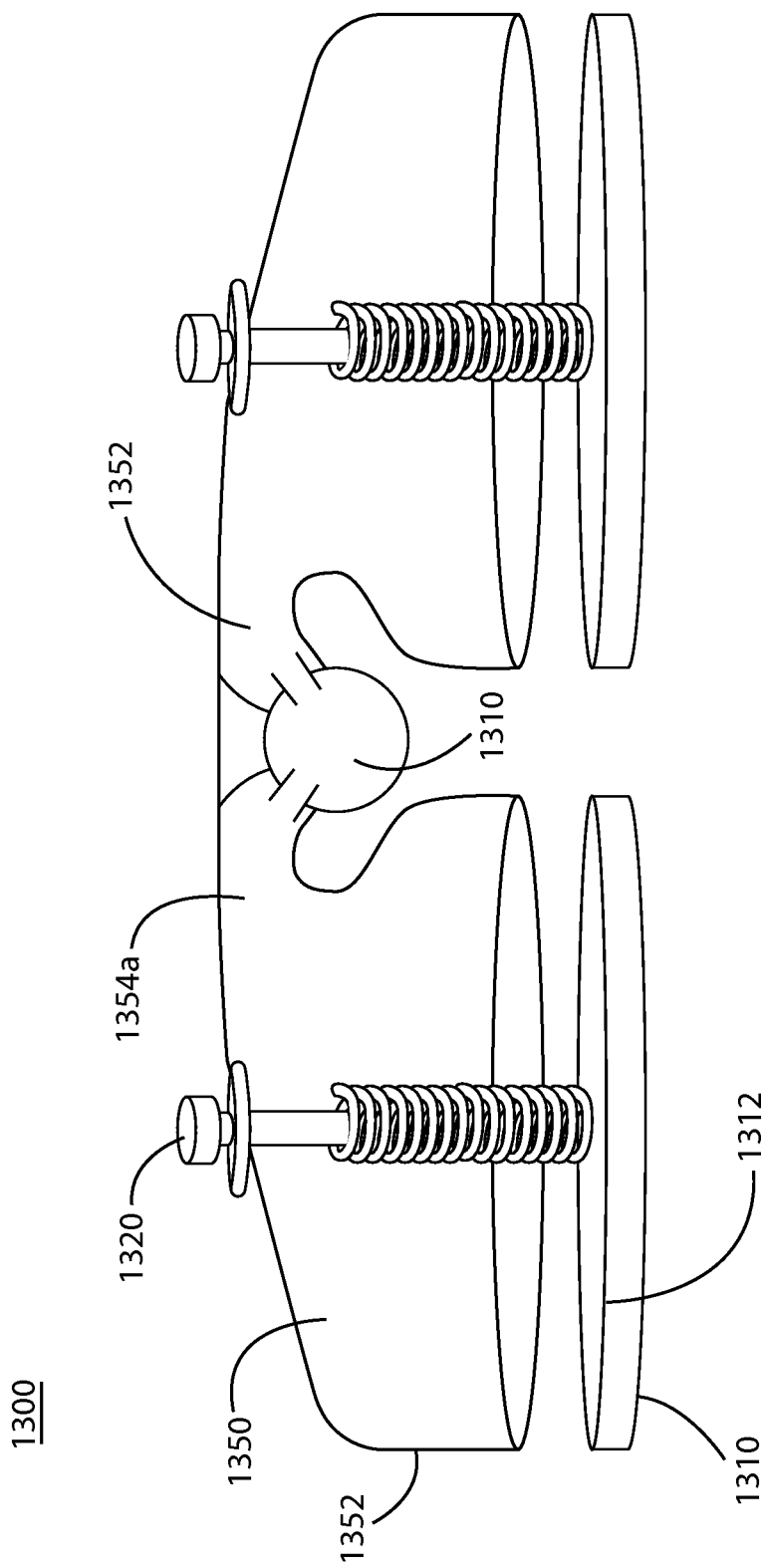
FIG. 13 shows an exemplary positive pressure chamber having percussive diaphragms in the exemplary PXT device of FIG. 7.
Figure 14:
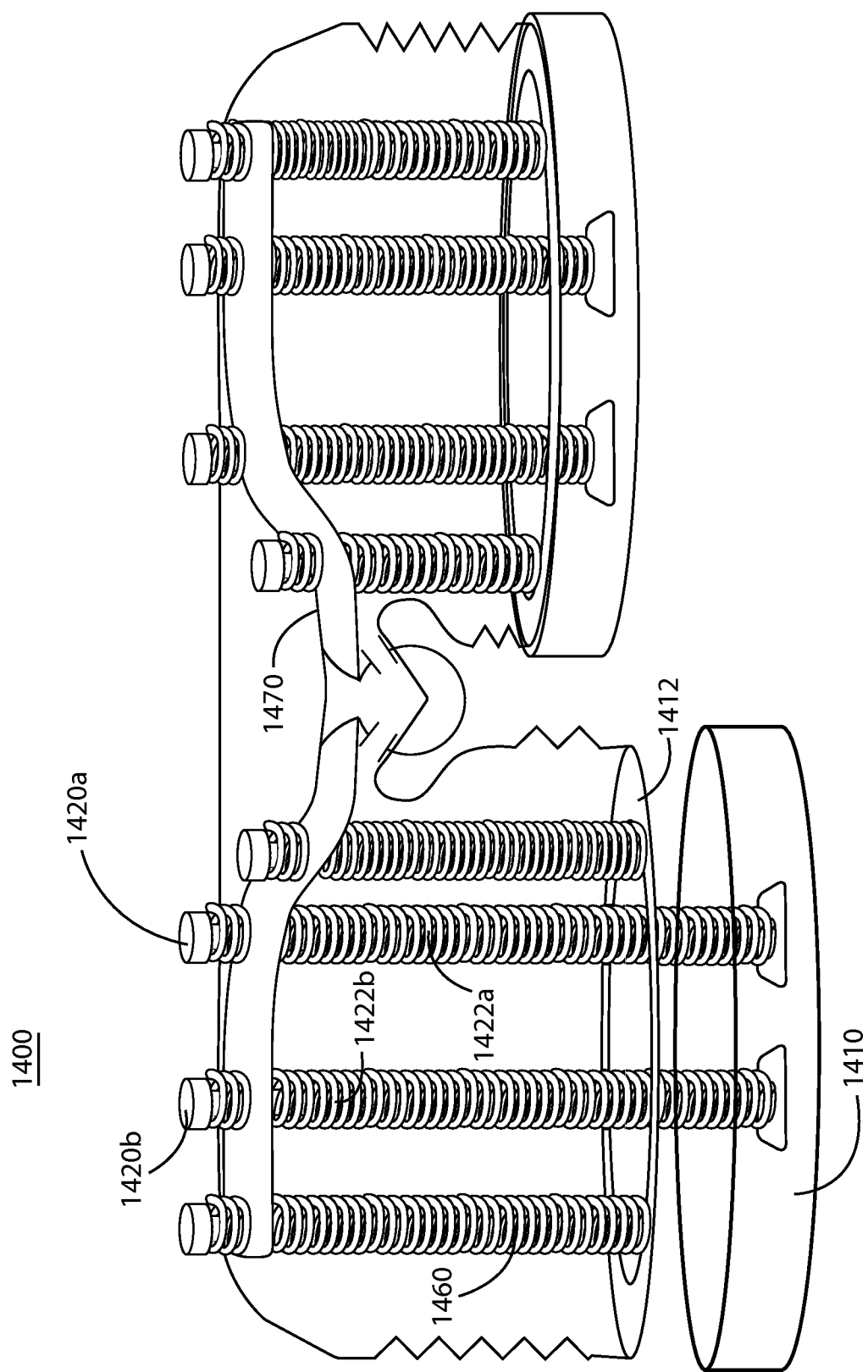
FIG. 14 shows another exemplary positive pressure chamber having percussive diaphragms.

Exemplary percussion chambers are shown in FIGS. 13 and 14. Each positive pressure or percussion chambers 750 may include an interior membrane or shell 1352 connected to a percussive diaphragm 1310 via one or more tension springs 1320. In a resting position, the percussive diaphragm is recessed from the membrane 730 to allow for chest expansion by the negative pressures. By directly fastening and lifting membrane/chest wall, both the tension springs 1320 and the negative force may work in unison for full chest expansion.

At peak FRC or inspiration, one might better simulate a cough reflex by applying percussion as well as downward movement of ribcage by the operator. This may be achieved by increasing the positive pressure in the chambers 1350 until the pressure reaches a point to overcome the force of the tension spring 1320, causing a pop-off of the percussive diaphragm 1310, which percusses the chest wall of the patient. Once pop-off occurs, the diaphragm 1310 may reset to its resting, recessed position.

The pop-off of the percussive diaphragm 1310 may cause enough gas to be released to possibly disrupt the negative pressure fields of the negative pressure chambers 740. In some embodiments, in order to alleviate these concerns and/or isolate the negative pressure in the chambers 740 from the positive pressure chambers 1350, the positive pressure chambers 1350 may be vented/open to ambient air to allow for air to escape, as described below As illustrated in FIG. 14, a percussion chamber 1450 may also include a tension bars 1470 and one or more support members 1460. The tension bars 1470 may lie superior to percussion chamber 1450. By elevating the tension bars 1470, it may be possible for an operator to set the resting position of the percussive diaphragms 1410 to allow for more or less chest expansion or more or less percussion. For example, the support members 1460 may be pleats to guide folding of chamber wall like an accordion or bellows.

As noted above, each chamber 1450 may be diamond-shaped in order to accommodate flexion during the tail wagging motion. This shape may allow the tail percussion chambers 1450 to move laterally both left and right relative to the divider block 780. The diamond shape may allow for better contour, rather than wider chambers 1450 that may restrict lateral movement. The percussion chambers 1450 may abut each other on either left or right lateral to divider block, or they may be physically separate. Lateral flexion may allow, for example, for targeting the bend of the left lung compared to the bend of the right lung. The space and volume lost when moving lateral may be lost in the vacuum chambers (VC), without sacrificing percussion surface area. The negative pressure chambers 640 may still be able to suction when compressed due to a rigid plastic stent that coats/lines the internal surface of the long membrane tubules, which interface with negative pressure ribs 740.

In some embodiments, the percussion chambers 1450 may be made of non-elastic rubber that does not distend (stretch) but instead may have pleats to allow for compression in desired positions in order to provide greater lift to the chest wall. Other materials also may be used. These pleats may allow for folding much like an accordion provides the creases that may allow for greater chest expansion by allowing the percussion diaphragms 1410 to become more recessed relative to chest wall thereby expanding Functional Residual Capacity (FRC) in the lungs.

The percussion chamber may be supported by a shell 1450 that is exceptional and separate from the outer shell 720 of the negative chambers 740. With the negative chamber ending at each diaphragm 1410, excess gas emitted during pop-off to vent out without interrupting/affecting the negative pressure seal in effect to chest wall. If positive pressure is not active with positive pressure chambers open to ambient air pressure, the positive pressure chambers above the diaphragms may be collapsed by increasing the tension in a control set of tension springs 1460, thereby raising/recessing the percussion chambers 1450 allowing for greater chest expansion. In the illustrated embodiment, the percussion rim 1412 may be raised or lowered to adjust the depth at with percussion chamber membrane diaphragm 1410 rests, with the desired tension at which pop-off occurs controlled by the tension in tension springs 1422*a-b* in conjunction with the specific psi gas sources 105. The height/depth of the control tension springs 1460 and the pop-off setting established by the tension springs 1422*a-b* may be adjusted manually or electronically, such as by electric motors coupled to the springs. Other mechanisms for establishing the height/depth of the percussion chamber 1450, the pressure required for pop-off, and/or controlling either feature may be used. The percussion chambers 1450 also may include ridges that define a channel between the negative pressure chambers and the positive pressure chambers. These channels may allow for the escape of air during pop-off.

There may be a variety of factors that determine the rate and/or force of the percussion applied by a PXT device 700. These factors include, for example, the psi of the source gas, the volume of the percussion chamber 1350 with diaphragm in closed (sealed) position, the amount of tension in the springs 1320 holding the diaphragm 1310 in place, and the control and distribution of gas to specific chambers 1350. Each of these exemplary factors is now explored.

The psi of the gas source may be adjusted to deliver any preferred psi less than about fifty PSI by using a gas regulator. Titration of the PSI may allow the health care provider to control the force that the percussion diaphragm 1310 exerts at pop-off, thereby transferring said force to chest wall. For example, less PSI with less tension in a smaller percussion chamber 1350 may deliver less force, which may be desirable, for example, for percussing a neonate's chest. For a larger patient, such as an adult patient, a higher PSI and/or higher tension in the springs 1320. In addition, the flow rate may be controlled more precisely using a flowmeter. Use of a flowmeter may allow the source gas to be administered in liters per minute or the like which could more accurately control the smaller volumes and pressures used in, for example, a premature baby, with smaller force transferred to patient.

The volume and/or the size of percussion chamber may correspond with the size of the patient. For example, as the neonate size is the smallest, the force of percussion may also be the least.

The tension springs 1520 may control the rate of pop-off/percussion. In the embodiment illustrated in FIG. 15, multiple tension springs 1520*a* and 1520*b* may be used for each chamber 1550 allowing for multiple percussions from one chamber. Recesses or cuts may be made at rim 1512 of percussion chamber 1550 to allowing for multiple percussion diaphragms to be computer controlled electronically.

In some embodiments, the tension springs 1420 may have a counter-force mechanism, essentially a bar 1470 that will begin a superior position relative to the spinal column that may be connected to and receive structural support from the positive pressure vertebrae. This positioning of the tension bar 1470 at an equal or higher position than the ribcage apexes will allow for the percussion diaphragm 1410, when desired, to be lifted away from chest wall, allowing for greater lung expansion and recruitment of atelectatic lung segments.

The distribution of precise gas pressures to individual selected chambers may be achieved through the spine. As noted above, the spine 710 may be honeycombed, allowing multiple pressure tubules within spine to be dedicated to a specific chamber. In some embodiment, a software program may be used to control psi delivered to each chamber 1350 and/or to adjust the tension in individual tension springs 1320 or the position of a percussive diaphragm via the support members 1360. This may allow for subdivision of the chambers 1350, in order to vary the percussion patterns i.e., a massage device. For example, percussion may be applied in various wave patterns or the like.

As noted above, various modes of operation may be provided. For example, a cough-assist mode may be provided. In a cough assist mode of operation, chest expansion may be facilitated by generating increasingly negative pressures while a percussion chamber is raised to a recessed position. This mode of operation may mimic a deep sigh breath in chest wall. Upon switching from inspiratory phase to expiratory phase, percussion may be applied and/or negative pressure may be disengaged to push/percuss chest wall, thereby "coughing" the patient chest wall.

Optionally, the inspiratory:expiratory ratio (I:E ratio) described in the previous paragraph may be synchronized to a positive pressure ventilator attached to patients airway. Synchronization of the PXT device may aide and contribute to more effective lung and airway recruitment for patients with lung collapse. Because the operator is not relying solely on positive pressure via mechanical ventilation, but instead combining the two forms of airway expansion, the provider may resolve the collapsed lung more effectively.

Another mode of operation that may be particularly useful for treating spontaneously breathing patients may involve percussion started in the lower airways (i.e. at tail end of PXT) and may be propulsed in an upward manner, thereby stimulating a cough reflex first in lower/smaller airways and then transferred moved in an upward direction out to larger airways. This wave pattern may be highly effective, for example, for airway clearance of cystic fibrosis patients.

While various embodiments of the invention have been described, it will be apparent to those of ordinary skill in the art that many more embodiments and implementations are possible within the scope of the invention. Accordingly, the invention is not to be restricted except in light of the attached claims and their equivalents.

I claim:

1. A medical device comprising:
   an inflow tube;
   an outflow tube;
   a shell that houses a negative pressure lumen operatively coupled to the outflow tube and a positive pressure chamber operatively coupled to the inflow tube, wherein the shell is generally contoured to the triangular shape of a single human lung within a chest wall;
   a membrane operatively coupled to the negative pressure lumen; and
   a handle connected to the shell.

2. The medical device of claim 1, where the membrane includes a substantially concave suction cup.

3. The medical device of claim 2, where the suction cup include an aperture that is operatively coupled to the negative pressure lumen.

4. The medical device of claim 3 further comprising a bicuspid valve disposed between the suction cup and the negative pressure lumen.

5. The medical device of claim 4, where the membrane include a quick release valve operatively coupled to the inflow tube.

6. The medical device of claim 1, where the shell is divided into segments including an apex segment, a medial segment, and a lower segment.

7. The medical device of claim 6, where the apex segment of the shell is substantially triangular.

8. The medical device of claim 6, further comprising a first positive pressure chamber and a divider block, where the positive pressure chamber is operatively coupled to the apex segment of the membrane, the first positive pressure chamber is operatively coupled to the medial segment of the membrane, and the divider block is disposed in the housing between the positive pressure chamber and the first positive pressure chamber.

9. The medical device of claim 6, further comprising a variable geometry front support coupled to the apex segment of the shell.

10. The medical device of claim 1, further comprising a rotatable handle attached to the inflow tube and the outflow tube, whereby rotation of the handle generates a torque that causes distortion of the membrane.

11. The medical device of claim 1, further comprising a first positive pressure chamber, where the positive pressure chamber may be pressurized independently of the first positive pressure chamber.

12. The medical device of claim 1, where the positive pressure chamber includes a percussive diaphragm that transfers a percussive force to the membrane when a pressure in the positive pressure chamber reaches a predetermined level.

13. The medical device of claim 1, further comprising a plurality of positive pressure chambers including the positive pressure chamber, where the inflow tube includes a plurality of outlets and a plurality of pressure tubes, where each of the plurality of outlets is operatively coupled to a corresponding one of the plurality of pressure tubes, wherein each of the plurality of pressure tubes are coupled to a corresponding one of the plurality positive pressure chambers.

14. The medical device of claim 13, further comprising a control system that can pressurize each of the plurality of positive pressure chambers in a predetermine pattern.

15. The medical device of claim 1, further comprising a plurality of negative pressure lumens cantilevered to form ribs.

16. A medical device comprising:
an inflow tube;
an outflow tube;
a shell that houses a plurality of negative pressure lumens operatively coupled to the outflow tube and a plurality of positive pressure chambers operatively coupled to the inflow tube, wherein the shell is generally contoured to the triangular shape of a single human lung within a chest wall;
a membrane including a plurality of suction cups, each of the plurality of suction cups operatively coupled to a corresponding one of the plurality negative pressure lumens; and
a handle connected to the shell.

17. The medical device of claim 16, where each of the plurality of positive pressure chambers can be pressurized independently of the other positive pressure chambers, each positive pressure chamber includes a percussive diaphragm that transfers a percussive force to the membrane when a pressure in the positive pressure chamber reaches a predetermined level.

18. The medical device of claim 17, further comprising a control system that can pressure each of the plurality of positive pressure chambers in a predetermine pattern.

19. A medical device comprising:
an inflow tube having a plurality of outlets and a plurality of pressure tubes, where each of the plurality of outlets is operatively coupled to a corresponding one of the plurality of pressure tubes;
an outflow tube;
a divider block coupled to the inflow tube and the outflow tube;
a shell that houses a plurality of negative pressure lumens operatively coupled to the outflow tube and a plurality of positive pressure chambers, each of the plurality of positive pressure chambers operatively coupled to a corresponding outlet of the inflow tube, where each of the plurality of positive pressure chambers can be pressurized independently of the other positive pressure chambers;
a membrane having an apex segment, a medial segment, and a lower segment, where each of the apex segment, the medial segment and the lower segment include a plurality of suction cups, each of the plurality of suction cups operatively coupled to a corresponding one of the plurality negative pressure lumens, where the divider block is coupled to the membrane between the apex segment and the medial segment; and
a rotatable handle attached to the inflow tube and the outflow tube, whereby rotation of the handle generates a torque that causes distortion of the membrane.

20. The medical device of claim 19, further comprising a control system that can pressurize each of the plurality of positive pressure chambers in a predetermine pattern.

* * * * *